United States Patent

Lavielle et al.

(10) Patent No.: US 6,747,032 B2
(45) Date of Patent: Jun. 8, 2004

(54) PYRIMIDIN-4-ONE COMPOUNDS

(75) Inventors: Gilbert Lavielle, La Celle Saint Cloud (FR); Thierry Dubuffet, Bolbec (FR); Olivier Muller, Pontoise (FR); Mark Millan, Le Pecq (FR); Anne Dekeyne, Cernay La Ville (FR); Mauricette Brocco, Paris (FR)

(73) Assignee: Les Laboratoires Servier, Courbevoie (FR)

( * ) Notice: Subject to any disclaimer, the term of this patent is extended or adjusted under 35 U.S.C. 154(b) by 0 days.

(21) Appl. No.: 10/125,188

(22) Filed: Apr. 18, 2002

(65) Prior Publication Data

US 2003/0087916 A1 May 8, 2003

(30) Foreign Application Priority Data

Apr. 18, 2001 (FR) .............................. 01 05216

(51) Int. Cl.[7] ................ C07D 519/00; A61K 31/519; A61P 25/18; A61P 25/24
(52) U.S. Cl. ................ 514/259.2; 544/278; 544/279; 544/281; 544/282; 514/259.41
(58) Field of Search ................ 544/278, 282, 544/279, 281; 514/259.2, 259.41

(56) References Cited

U.S. PATENT DOCUMENTS 6,511,987 B1   1/2003   Yuan et al. ............ 514/292

OTHER PUBLICATIONS

Blier et al. (Biol. Pyschiatry 2003; 53: 193–203).*
Sara, et al., *Behavioral and Neural Biology*, 51:401–411 (1989).
Smith, et al., *J. Psychopharmacology*, 6(3):376–381 (1991).
Coull, et al., *Psychopharmacology*, 123: 239–249 (1996).
Pascual, et al., *Neuroscience Letters*, 142: 36–40 (1992).
Tellez, et al., *Eur J Pharmacology*, 277: 113–116 (1995).
Sirvio, et al., *Pharmacology, Biochemistry, and Behavior*, 45:123–129 (1993).
Haapalinna, et al., *Eur J Pharmacology*, 347:29–40 (1998).
Chopin, et al., *J Pharmacology and Experimental Therapeutics*, 301:187–196 (2002).
Millan, et al., *European J Neuroscience*, 12: 1079–1095 (2000).
De Boer, et al., *J of Pharmacology and Experimental Therapeutics*, 277: 852–860 (1996).
Haddjeri, et al., *Naunyn–Schmiedeberg's Arch Pharmacol*, 355: 20–29 (1997).
Koskinen, et al., Pharmacology, Biochemistry and Behavior, 66(4): 729–738 (2000).
Millan, et al., J Pharmacology and Experimental Therapeutics, 298:581–591 (2001).
Chopin, et al., *j. Pharmacology and Experimental Therapeutics*, 288:798–804 (1999).
Bezard, et al., *Prog. Neuro–Psychopharmacol. & Biol. Psychiat.*, 23:1237–1246 (1999).
*Pharmaprojects*, Accession No. 3266.

* cited by examiner

Primary Examiner—Mark L. Berch
Assistant Examiner—Kahsay Habte
(74) Attorney, Agent, or Firm—The Firm of Hueschen and Sage

(57) ABSTRACT

Compound of formula (I):

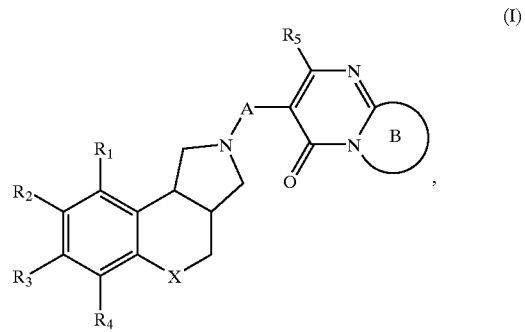

wherein:

$R_1$, $R_2$, $R_3$ and $R_4$, which may be the same or different, each represent a hydrogen atom, a halogen atom or a group selected from alkyl, alkoxy, polyhaloalkyl, hydroxy, cyano, nitro and amino, or $R_1$ with $R_2$, $R_2$ with $R_3$, or $R_3$ with $R_4$, together with the carbon atoms carrying them, form an optionally substituted benzene ring or an optionally substituted heteroaromatic ring, X represents an oxygen atom or a methylene group, A represents an alkylene chain,

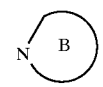

represents an optionally substituted, unsaturated, nitrogen-containing heterocycle and $R_5$ represents an alkyl group, its enantiomers and diastereoisomers, and addition salts thereof with a pharmaceutically acceptable acid, a medicinal products containing the same are useful as a double $\alpha_2$/5-$HT_{2c}$ antagonist.

13 Claims, No Drawings

PYRIMIDIN-4-ONE COMPOUNDS

SUMMARY OF THE INVENTION

The present invention relates to new pyrimidin-4-one compounds, and to pharmaceutical compositions containing them.

The invention relates also to their use as combined $\alpha_2/5\text{-HT}_{2c}$ ligands.

DESCRIPTION OF THE PRIOR ART 1,2,3,3a,4,9b-Hexahydrochromeno[3,4-c]pyrrole compounds have been described in Patent Application EP 691 342 in terms of their serotoninergic antagonist character and in Patent Application EP 887 350 in terms of their $D_3$ dopaminergic ligand character.

BACKGROUND OF THE INVENTION

The corticolimbic structures play an essential part in the processes controlling the altered functions in psychiatric disorders. In particular, it is now recognised that disturbance of monoaminergic transmission is strongly implicated in the aetiology of those various disorders. For example, in the case of depression, monoaminergic activity is reduced in the frontal cortex, the hippocampus and the nucleus accumbens.

Among the various classes of auto- and hetero-receptors of monoamines implicated in the mechanisms of regulation, $\alpha_2$-AR (autoreceptor) and $5\text{-HT}_{2c}$ receptors have been found to be of major importance. Those two receptor sub-types act in the same direction by inhibiting dopaminergic and adrenergic transmission. On the one hand, retro-control is exerted by $\alpha_2$-AR (autoreceptor) receptors on noradrenergic neurons (J. Pharmacol. Exp. Ther., 1994, 270, 958), and, on the other hand, $\alpha_2$-AR receptors and $5\text{-HT}_{2c}$ heteroreceptors exert inhibitory control on dopaminergic and noradrenergic transmission (Neuropharmacology, 1997, 36, 609, J. Psychopharmacol. 2000, 14 (2), 114–138).

Compounds binding to one or other of those receptor sub-types have, in the past, demonstrated their potential for the treatment of a number of pathologies.

For example, the beneficial role of $\alpha_2$-AR antagonist compounds has been studied in the treatment of cognitive disorders (J. Pharmacol., 1992, 6, 376), Parkinson's disease (CNS Drugs, 1998, 10, 189), schizophrenia (Science 1999, 286, 105–107), depression (J. Psychopharmacol. 1996, 10 Suppl. 3, 35–42), disturbances of libido, and sexual dysfunctions (J. Pharmacol., 1997, 11, 72). Likewise, $5\text{-HT}_{2c}$ receptor ligands have demonstrated their usefulness in the treatment of sexual dysfunctions (J. Pharmacol., ibid.) and Parkinson's disease (Drug News Perspect., 1999, 12, 477), as well as anxiety (Br. J. Pharmacol., 1996, 117, 427), depression (Pharmacol. Biochem. Behav. 1988, 29, 819–820), impulsive disorders (Biol. Psych. 1993, 33, 3–14), appetite disorders (British J. Pharmacol. 1998, 123, 1707–1715), sleep disorders (Neuropharmacology 1994, 33 (3/4), 467–471) and schizophrenia (Neurosci. Lett., 1996, 181, 65).

Compounds having a double $\alpha_2$-AR and $5\text{-HT}_{2c}$ antagonist character may be highly useful to clinicians in obtaining, by administration of a single compound, a reinforced action whilst improving tolerability. A compound of that kind, moreover, has a considerable advantage over the administration of two different compounds.

The compounds of the invention have a novel structure providing them with their double $\alpha_2/5\text{-HT}_{2c}$ antagonist character and are therefore useful in the treatment of depression, impulsive behaviour disorders, anxiety, schizophrenia, Parkinson's disease, cognitive disorders, disturbances of libido, sexual dysfunctions, appetite disorders and sleep disorders.

DETAILED DESCRIPTION OF THE INVENTION

The present invention relates to compounds of formula (I):

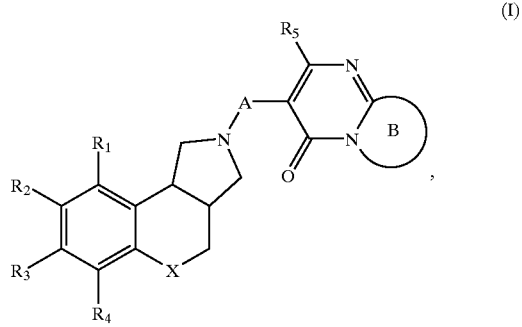

wherein:
$R_1$, $R_2$, $R_3$ and $R_4$, which may be the same or different, each represent a hydrogen atom, a halogen atom or a group selected from linear or branched $(C_1-C_6)$alkyl, linear or branched $(C_1-C_6)$alkoxy, linear or branched $(C_1-C_6)$polyhaloalkyl, hydroxy, cyano, nitro and amino, or $R_1$ with $R_2$, $R_2$ with $R_3$, or $R_3$ with $R_4$, together with the carbon atoms carrying them, form an optionally substituted benzene ring or an optionally substituted heteroaromatic ring, X represents an oxygen atom or a methylene group,
A represents a linear or branched $(C_1-C_6)$alkylene chain,

represents an unsaturated nitrogen-containing heterocycle optionally substituted by one or two identical or different substituents selected from halogen atoms and linear or branched $(C_1-C_6)$alkyl, hydroxy, linear or branched $(C_1-C_6)$alkoxy, linear or branched $(C_1-C_6)$ polyhaloalkyl, cyano, nitro, amino, optionally substituted phenyl, optionally substituted thienyl, optionally substituted furyl and optionally substituted pyrrolyl groups, and $R_5$ represents a linear or branched $(C_1-C_6)$alkyl group,
to their enantiomers and diastereoisomers, and to addition salts thereof with a pharmaceutically acceptable acid or base,
it being understood that:
the term "$(C_1-C_6)$alkyl" denotes a hydrocarbon chain containing from one to six carbon atoms,
the term "$(C_1-C_6)$alkoxy" denotes a $(C_1-C_6)$alkyl-oxy group containing from one to six carbon atoms,
the term "$(C_1-C_6)$alkylene" denotes a bivalent hydrocarbon chain containing from one to six carbon atoms, the term $(C_1-C_6)$polyhaloalkyl denotes a carbon chain containing from one to six carbon atoms and from 1 to 9 halogen atoms, the term "heteroaromatic ring" denotes a 5- or 6-membered aromatic ring containing one, two or three hetero atoms selected from oxygen, nitrogen and sulphur, the term "unsaturated nitrogen-containing heterocycle" denotes a 5- to 7-membered unsaturated ring having one, two or three unsaturations and containing one, two or three hetero atoms, one of those hetero atoms being the nitrogen atom and the additional hetero atom(s) optionally present being selected from oxygen, nitrogen and sulphur atoms, the term "optionally substituted" applied to the expressions "benzene ring", "heteroaromatic ring", "phenyl", "thienyl", "furyl" or pyrrolyl" indicates that those groups are optionally substituted by one or two identical or different substituents selected from halogen atoms and linear or branched $(C_1-C_6)$alkyl, hydroxy, linear or branched $(C_1-C_6)$alkoxy, linear or branched $(C_1-C_6)$polyhaloalkyl, cyano, nitro and amino groups.

Among the pharmaceutically acceptable acids there may be mentioned, without implying any limitation, hydrochloric acid, hydrobromic acid, sulphuric acid, phosphoric acid, acetic acid, trifluoroacetic acid, lactic acid, pyruvic acid, malonic acid, succinic acid, glutaric acid, fumaric acid, tartaric acid, maleic acid, citric acid, ascorbic acid, methanesulphonic acid, camphoric acid, oxalic acid etc.

Among the pharmaceutically acceptable bases there may be mentioned, without implying any limitation, sodium hydroxide, potassium hydroxide, triethylamine etc.

Among the heteroaromatic rings there may be mentioned, without implying any limitation, thiophene, pyridine, furan, pyrrole, imidazole, oxazole, isoxazole, thiazole, isothiazole, pyrimidine.

Preferred unsaturated nitrogen-containing heterocycles are 1,2-dihydropyridine, 2,3-dihydro-1,3-thiazole and 2,3-dihydro-oxazole.

A (3aα,9bα) or (3aβ,9bβ) compound is understood to mean a compound wherein the relevant ring junction is of the cis configuration.

A (3aα,11cα) or (3aβ,11cβ) compound is understood to mean a compound wherein the relevant ring junction is of the cis configuration.

A (3aα,9bβ) or (3aβ,9bα) compound is understood to mean a compound wherein the relevant ring junction is trans.

A (3aα,11cβ) or (3aβ,11cα) compound is understood to mean a compound wherein the relevant ring junction is trans.

In preferred compounds of formula (I), $R_1$, $R_2$, $R_3$ and $R_4$, which may be the same or different, each represent a hydrogen atom or a linear or branched $(C_1-C_6)$alkyl, linear or branched $(C_1-C_6)$alkoxy or hydroxy group.

Preferred compounds of the invention are those wherein $R_1$ and $R_2$, together with the carbon atoms carrying them, form a benzene ring and $R_3$ and $R_4$ each represent a hydrogen atom.

X preferably represents an oxygen atom.

The invention advantageously relates to compounds of formula (I) wherein A represents an ethylene, propylene or butylene chain.

The invention more especially relates to compounds of formula (I) wherein

represents the following group

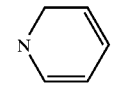

optionally substituted by one or two identical or different substituents selected from halogen atoms and linear or branched $(C_1-C_6)$alkyl, hydroxy, linear or branched $(C_1-C_6)$alkoxy, linear or branched $(C_1-C_6)$polyhaloalkyl, cyano, nitro, amino and thienyl groups.

Other preferred compounds of the invention are compounds of formula (I) wherein

represents the following group

optionally substituted by one or two identical or different substituents selected from halogen atoms and linear or branched $(C_1-C_6)$alkyl, hydroxy, linear or branched $(C_1-C_6)$alkoxy, linear or branched $(C_1-C_6)$polyhaloalkyl, cyano, nitro and amino groups.

The present invention more especially relates to compounds of formula (I) wherein A represents an ethylene chain, X represents an oxygen atom, $R_5$ represents a methyl group and

represents the following group

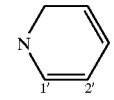

optionally substituted in the 2'-position by a halogen atom or a group selected from linear or branched $(C_1-C_6)$alkyl, cyano and thienyl.

The invention relates most especially to the following compounds:

3-[2-((3aα,9bα)-9-methoxy-1,3a,4,9b-tetrahydrochromeno[3,4-c]pyrrol-2 (3H)-yl)-ethyl]-2-methyl-4H-pyrido[1,2-a]pyrimidin-4-one, 3-[2-((3aα,11cα)-1,3a,4,11c-tetrahydrobenzo[5,6]chromeno[3,4-c]pyrrol-2(3H)-yl-ethyl]-2-methyl-4H-pyrido[1,2-a]pyrimidin-4-one, and 3-[2-((3aβ,11cα)-1,3a,4,11c-tetrahydrobenzo[5,6]chromeno[3,4-c]pyrrol-2 (3H)-yl)ethyl]-2-methyl-4H-pyrido[1,2-a]pyrimidin-4-one.

The invention relates also to a process for the preparation of compounds of formula (I), which process is characterised in that a compound of formula (II):

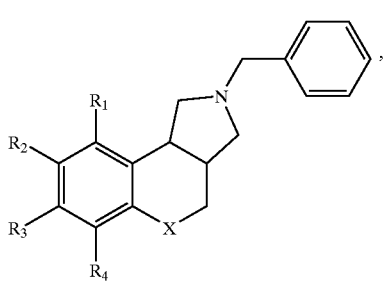

(II)

wherein $R_1$, $R_2$, $R_3$, $R_4$ and X are as defined for formula (I),
is subjected to catalytic hydrogenation to yield the compound of formula (III):

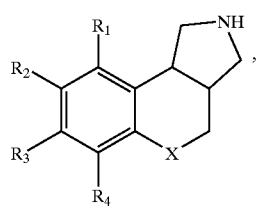

(III)

wherein $R_1$, $R_2$, $R_3$, $R_4$ and X are as defined hereinbefore, which is reacted either with a compound of formula (IV):

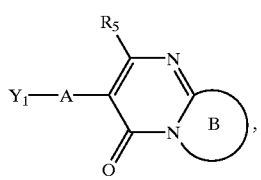

(IV)

wherein A, B and $R_5$ are as defined for formula (I) and $Y_1$ represents a leaving group such as, for example, a halogen atom or a tosylate, triflate or mesylate group, or, under conditions of reductive amination, with a compound of formula (V):

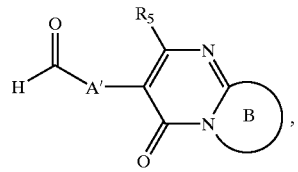

(V)

wherein B and $R_5$ are as defined for formula (I) and A' represents a bond or a linear or branched ($C_1$–$C_5$) alkylene chain,
to yield the compound of formula (I), which is purified, if necessary, according to a conventional purification technique, which is separated, if desired, into its stereoisomers according to a conventional separation technique, and which is converted, if desired, into addition salts thereof with a pharmaceutically acceptable acid or base.

The compounds of formula (II) wherein X represents an oxygen atom (compounds of formula (IIa)) may be obtained starting from the compound of formula (VI):

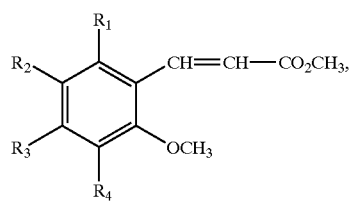

(VI)

wherein $R_1$, $R_2$, $R_3$ and $R_4$ are as defined hereinbefore, which is subjected to cycloaddition with N-benzyl-N-(methoxymethyl)-trimethylsilylmethylamine under conditions described by K. Achiwa et al. (Chem. Pharm. Bull. 1985, 33 (7), 2762–66), to yield the compound of formula (VII):

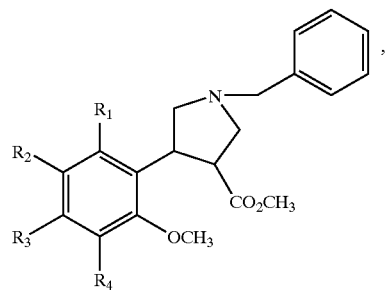

(VII)

wherein $R_1$, $R_2$, $R_3$ and $R_4$ are as defined hereinbefore, which is then converted, by reduction followed by deprotection of the phenol function, into the compound of formula (VIII):

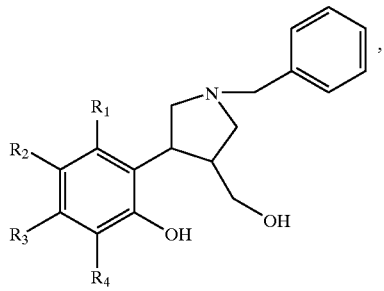

(VIII)

wherein $R_1$, $R_2$, $R_3$ and $R_4$ are as defined hereinbefore, which is then converted into the compound of formula (IIa) by a Mitsunobu reaction.

The configuration of the ring junction of the compound of formula (IIa) thereby obtained is determined by the configuration (Z or E) of the compound of formula (VI) used.

The compounds of formula (IIa) may also be obtained starting from the compound of formula (IX):

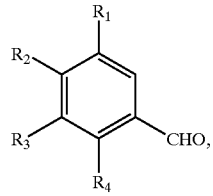
(IX)

wherein $R_1$, $R_2$, $R_3$ and $R_4$ are as defined hereinbefore, which is oxidised into the compound of formula (X):

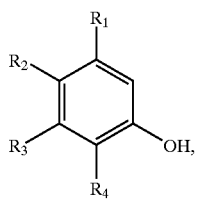
(X)

wherein $R_1$, $R_2$, $R_3$ and $R_4$ are as defined hereinbefore, which is reacted with methyl propiolate to yield the coumarin of formula (XI):

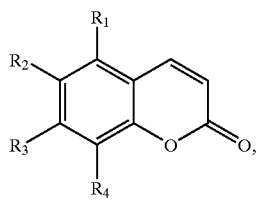
(XI)

wherein $R_1$, $R_2$, $R_3$ and $R_4$ are as defined hereinbefore, which is subjected:

- either, when it is desired to prepare a compound of formula (IIa) wherein the ring junction is trans, to reaction with sodium methanolate and then to a cycloaddition reaction with N-benzyl-N-(methoxymethyl)-trimethylsilylmethylamine under conditions described by K. Achiwa et al. (Chem. Pharm. Bull. 1985, 33 (7), 2762–66), followed by a reduction reaction,
  to yield a compound of formula (VIII) whose configuration is trans,
  which is then converted into a trans compound of formula (IIa) by a Mitsunobu reaction,
- or, when it is desired to prepare a compound of formula (IIa) wherein the ring junction is cis, to a cycloaddition reaction with N-benzyl-N-(methoxymethyl)-trimethylsilylmethylamine under conditions described by K. Achiwa et al. (Chem. Pharm. Bull. 1985, 33 (7), 2762–66), to yield the compound of formula (XII) whose ring junction is cis:

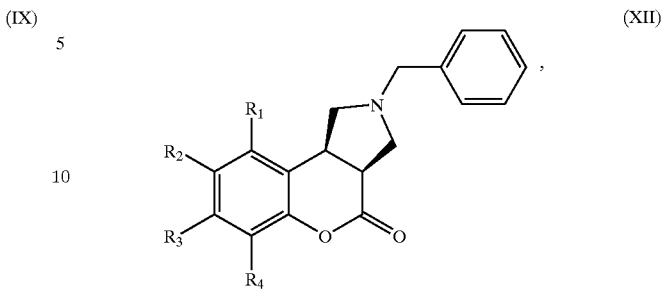
(XII)

wherein $R_1$, $R_2$, $R_3$ and $R_4$ are as defined hereinbefore, which is then reduced to form a compound of formula (VIII) whose configuration is cis, which is then converted into a cis compound of formula (IIa) by a Mitsunobu reaction.

The compounds of formula (II) wherein X represents a methylene group (compounds of formula (IIb)) may be obtained starting from the compound of formula (XIII):

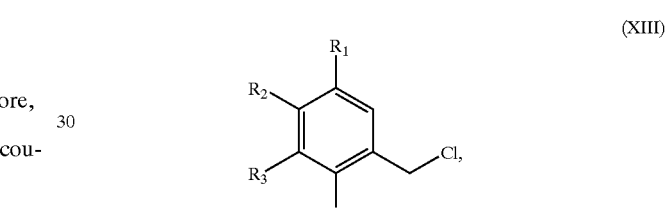
(XIII)

wherein $R_1$, $R_2$, $R_3$ and $R_4$ are as defined for formula (I), which is reacted with ethyl acrylate to yield the compound of formula (XIV):

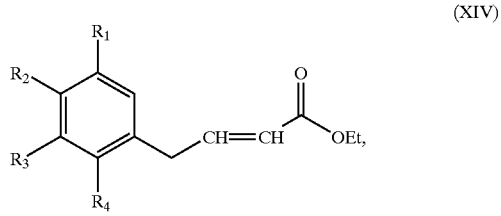
(XIV)

wherein $R_1$, $R_2$, $R_3$ and $R_4$ are as defined hereinbefore, which is converted, by reduction followed by hydrolysis, into the compound of formula (XV):

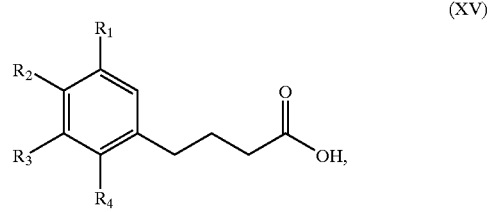
(XV)

wherein $R_1$, $R_2$, $R_3$ and $R_4$ are as defined hereinbefore, which is cyclised to form the compound of formula (XVI):

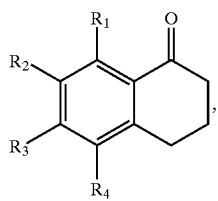
(XVI)

wherein $R_1$, $R_2$, $R_3$ and $R_4$ are as defined hereinbefore, which is then converted into the compound of formula (XVII):

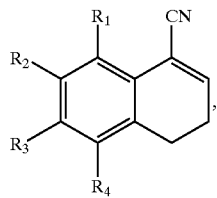
(XVII)

wherein $R_1$, $R_2$, $R_3$ and $R_4$ are as defined hereinbefore, and then, by addition of lithium cyanide, into the compound of formula (XVIII):

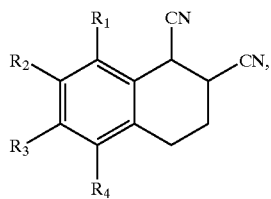
(XVIII)

wherein $R_1$, $R_2$, $R_3$ and $R_4$ are as defined hereinbefore, the cyano groups of which are converted into carboxy groups before being condensed to yield the compound of formula (XIX):

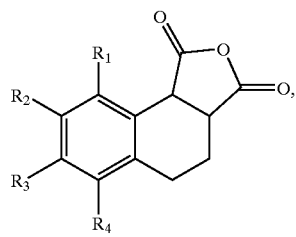
(XIX)

wherein $R_1$, $R_2$, $R_3$ and $R_4$ are as defined hereinbefore, which is then reacted with benzylamine to yield the compound of formula (XX):

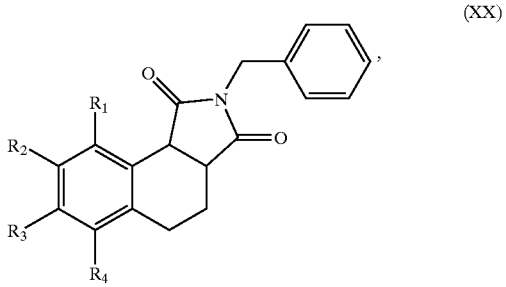
(XX)

wherein $R_1$, $R_2$, $R_3$ and $R_4$ are as defined hereinbefore, which is converted, by reduction, into the compound of formula (IIb).

The present invention relates also to pharmaceutical compositions comprising as active ingredient a compound of formula (I) together with one or more inert, non-toxic, pharmaceutically acceptable excipients. Among the pharmaceutical compositions according to the invention there may be mentioned more especially those that are suitable for oral, parenteral (intravenous, intramuscular or subcutaneous) or nasal administration, tablets or dragées, sublingual tablets, gelatin capsules, lozenges, suppositories, creams, ointments, dermal gels, injectable preparations, drinkable suspensions etc.

The useful dosage can be varied according to the nature and severity of the disorder, the administration route and also the age and weight of the patient and any associated treatments. The dosage varies from 0.5 mg to 2 g per 24 hours in one or more administrations.

The following Examples illustrate the invention but do not limit it in any way.

The starting materials used are known products or are prepared according to known methods of preparation.

The structures of the compounds described in the Examples have been determined by conventional spectrometric techniques (infra-red, NMR, mass spectrometry).

EXAMPLE 1

3-[2-((3aα,9bα)-9-Methoxy-1,3a,4,9b-tetrahydrochromeno[3,4-c]-pyrrol-2(3H)-yl)-ethyl]-2-methyl-4H-pyrido[1,2-a]pyrimidin-4-one dihydrochloride Step A: Methyl (3α,4α)-1-benzyl-4-(2,6-dimethoxyphenyl)-3-pyrrolidine-carboxylate To a solution, cooled to 5° C., containing 120 mmol of cis-(2,6-dimethoxy)cinnamic acid methyl ester and 0.1 ml of trifluoroacetic acid in 150 ml of ethyl acetate there are slowly added 100 mmol of N-benzyl-N-(methoxymethyl)trimethylsilylmethylamine. The reaction mixture is heated from 30° C. to 55° C. over 75 minutes. 0.75 g of potassium carbonate is then added and the mixture is stirred for 15 minutes. After filtering and evaporating off the solvents, the residue is taken up in 100 ml of ethyl acetate and the solution is heated at 50° C. 110 mmol of oxalic acid dissolved in 100 ml of acetone are then added, with vigorous stirring which is continued for 15 hours. After filtering and then washing with ether, the oxalate obtained is treated with two equivalents of 1N potassium hydroxide solution to yield the expected product.

Step B: (3α,4α)-1-Benzyl-3-hydroxymethyl-4-(2,6-dimethoxyphenyl)-pyrrolidine

To 120 mmol of lithium aluminium hydride suspended in 800 ml of tetrahydrofuran at +5° C. there are added 100 mmol of the compound obtained in the previous Step dissolved in 400 ml of tetrahydrofuran. After stirring for one hour at that temperature, the mixture is treated by the slow addition of 11 ml of water, 15 ml of 2N sodium hydroxide solution and 26 ml of water. The mixture is stirred for 10 hours and then filtered. The solvent is evaporated off to yield the expected product.

Step C: (3α,4α)-1-Benzyl-3-hydroxymethyl-4-(2,6-dihydroxyphenyl)-pyrrolidine

To 8.9 mmol of the compound obtained in the previous Step in 170 ml of dichloromethane there are added 44.5 ml of a 1M solution of boron tribromide in dichloromethane. The reaction mixture is heated at reflux for 8 hours and then treated with concentrated sodium hydroxide solution for one hour. The mixture is then neutralised using hydrochloric acid. After extracting with dichloromethane, the expected product is obtained after purification of the residue by chromatography on silica (eluant: dichloromethane/methanol 95/5).

Step D: (3aα,9bα)-2-Benzyl-9-hydroxy-1,2,3,3a,4,9b-hexahydrochromeno[3,4-c]-pyrrole Hydrochloride To 80 mmol of the compound obtained in the previous Step in 1 liter of tetrahydrofuran there are added, in succession, 120 mmol of diethyl azodicarboxylate and 120 mmol of triphenylphosphine. The mixture is stirred at ambient temperature for 15 hours. The solvent is evaporated off, and the crude product is taken up in 1 liter of isopropyl ether and heated at reflux for one hour. The precipitate obtained is removed and the filtrate is concentrated before being chromatographed (eluant: cyclohexane/ethyl acetate 70/30). The product obtained is converted into a salt using hydrochloric acid.

Step E: (3aα,9bα)-2-Benzyl-9-methoxy-1,2,3,3a,4,9b-hexahydrochromeno[3,4-c]-pyrrole Hydrochloride 11.6 mmol of the compound obtained in the previous Step in 50 ml of dimethylformamide are added to a solution containing 14 mmol of sodium hydride in 50 ml of dimethylformamide. After stirring for 30 minutes, 11.6 mmol of methyl iodide are added. After 1 hour at ambient temperature and then hydrolysis, the solvents are evaporated off. The residue is then taken up in water. After extraction with ether, drying and evaporation, the expected product is obtained after purification of the residue by chromatography on a silica column using a mixture of cyclohexane/ethyl acetate (75/25) as eluant.

Elemental Microanalysis:

|  | C % | H % | N % | Cl % |
| --- | --- | --- | --- | --- |
| calculated | 68.77 | 6.68 | 4.22 | 10.68 |
| found | 68.66 | 4.48 | 4.45 | 10.97 |

Step F. (3aα,9bα)-9-Methoxy-1,2,3,3a,4,9b-hexahydrochromeno[3,4-c]pyrrole 50 mmol of the compound obtained in the previous Step are dissolved in a mixture of 200 ml of methanol and 50 ml of water. 50 mmol of a 5N solution of hydrochloric acid in ethanol are added. After adding 2 grams of palladium dihydroxide, the reaction mixture is placed under an atmosphere of hydrogen. After the theoretical volume of hydrogen has been absorbed, the catalyst is filtered off and the filtrate is evaporated. The residue obtained is treated with 1N sodium hydroxide solution and extracted with dichloromethane to yield the expected product.

Step G: 3-[2-((3aα,9bα)-9-Methoxy-1,3a,4,9b-tetrahydrochromeno[3,4-c]-pyrrol-2(3H)-yl)-ethyl]-2-methyl-4H-pyrido[1,2-a]pyrimidin-4-one dihydrochloride To 7 mmol of the compound obtained in the previous Step in 100 ml of acetonitrile there are added 7 mmol of potassium carbonate. The mixture is heated to 60° C. 7 mmol of 3-(2-chloroethyl)-2-methylpyrido[1,2-a]pyrimidin-4-one (prepared according to Liebigs Ann. Chem. 1973, 103–110) are then added all at once. The mixture is heated at 80° C. for 18 hours. After cooling and adding water, the mixture is extracted with dichloromethane and then washed and dried. After filtering and evaporating off the solvents, the residue obtained is purified by chromatography on silica (eluant: dichloromethane/methanol 95/5). The product obtained is converted into a salt using hydrochloric acid.

Elemental Microanalysis:

|  | C % | H % | N % | Cl % |
| --- | --- | --- | --- | --- |
| calculated | 59.49 | 5.86 | 9.05 | 15.27 |
| found | 59.57 | 5.89 | 9.09 | 15.41 |

EXAMPLE 2

3-[2-((3aα,9bα)-6,8-Dimethoxy-7-methyl-1,3a,4,9b-tetrahydro-chromeno[3,4-c]pyrrol-2(3H)-yl)-ethyl]-2-methyl-4H-pyrido[1,2-a]-pyrimidin-4-one Sesquifumarate Step A: 2,4-Dimethoxy-3-methyl-phenol To 416 mmol of 2,4-dimethoxy-3-methyl-benzaldehyde dissolved in 200 ml of dichloromethane there are added 624 mmol of meta-chloroperbenzoic acid. The reaction mixture is heated at reflux for 5 hours before being filtered. The filtrate is washed three times using 200 ml of saturated NaHCO₃ solution each time and then dried over magnesium sulphate. After evaporating off the solvent, the crude product is taken up in 400 ml of methanol. 624 mmol of 10% KOH solution are added. The mixture is stirred for one hour and is then adjusted to pH=4 using 1N hydrochloric acid solution. After stirring for one hour, the volume is reduced to ⅓. The crude product is taken up in 400 ml of water and extracted with dichloromethane. The organic phases are collected and dried. After evaporating off the solvents, the residue obtained is purified by chromatography on a silica column (eluant: cyclohexane/ethyl acetate 90/10) to yield the expected product.

Step B: 6,8-Dimethoxy-7-methyl-coumarin

To 270 mmol of the compound obtained in the previous Step dissolved in 500 ml of anhydrous methanesulphonic acid there are added 270 mmol of methyl propiolate. The reaction mixture is heated at 90° C. for 30 minutes and then cooled to 0° C. After slowly adding water, the mixture is extracted with dichloromethane. The organic phases are collected, washed with 1N sodium hydroxide solution and then dried. After evaporating off the solvents, the residue obtained is triturated in ethyl ether and then filtered to yield the expected product.

Step C: (3α,4α)-1-Benzyl-3-hydroxymethyl-4-(3,5-dimethoxy-2-hydroxy-4-tolyl)-pyrrolidine The expected product is obtained according to the procedure described in Steps A and B of Example 1, starting from the compound obtained in the previous Step.

Step D: (3aα,9bα)-2-Benzyl-6,8-dimethoxy-7-methyl-1,2, 3,3a,4,9b-hexahydro-chromeno[3,4-c]pyrrole Hydrochloride The expected product is obtained according to the procedure described in Step D of Example 1, starting from the compound obtained in the previous Step.

Elemental Microanalysis:

|  | C % | H % | N % | Cl % |
|---|---|---|---|---|
| calculated | 67.10 | 6.97 | 3.73 | 9.43 |
| found | 66.90 | 7.00 | 3.92 | 9.57 |

Step E: (3aα,9bα)-6,8-Dimethoxy-7-methyl-1,2,3,3a,4,9b-hexahydro-chromeno-[3,4-c]pyrrole The expected product is obtained according to the procedure described in Step F of Example 1, starting from the compound obtained in the previous Step.

Step F: 3-[2-((3aα,9bα)-6,8-Dimethoxy-7-methyl-1,3a,4,9b-tetrahydro-chromeno-[3,4-c]pyrrol-2(3H)-yl)-ethyl]-2-methyl-4H-pyrido[1,2-a]pyrimidin-4-one sesquifumarate The expected product is obtained according to the procedure described in Step G of Example 1, starting from the compound obtained in the previous Step. The product obtained is converted into a salt using fumaric acid.

Elemental Microanalysis:

|  | C % | H % | N % |
|---|---|---|---|
| calculated | 61.07 | 5.80 | 6.89 |
| found | 61.73 | 6.03 | 7.19 |

EXAMPLE 3

3-[2-(1,3a,4,11c-Tetrahydrobenzo[5,6]chromeno[3,4-c]pyrrol-2(3H)-yl)-ethyl]-2-methyl-4H-pyrido[1,2-a]pyrimidin-4-one Fumarate Step A: 1,2,3,3a,4,11c-Hexahydrobenzo[5,6]chromeno[3,4-c]pyrrole The expected product is obtained according to the procedure described in Steps C to F of Example 2, starting from benzo[f]chromen-3-one.

Step B: 3-[2-(1,3a,4,11c-Tetrahydrobenzo[5,6]chromeno[3,4-c]pyrrol-2(3H)-yl)-ethyl -2-methyl-4H-pyrido[1,2-a]pyrimidin-4-one Fumarate The expected product is obtained according to the procedure described in Step G of Example 1, starting from the compound obtained in the previous Step.

Elemental Microanalysis:

|  | C % | H % | N % |
|---|---|---|---|
| calculated | 68.30 | 5.54 | 7.96 |
| found | 67.87 | 5.57 | 7.79 |

EXAMPLE 4

6-[2-((3aα,11cα)-1,3a,4,11c-Tetrahydrobenzo[5,6]chromeno[3,4-c]-pyrrol-2(3H)-yl]-ethyl]-7-methyl-5H-[1,3]thiazolo[3,2-a]pyrimidin-5-one Fumarate The expected product is obtained according to the procedure described in Step G of Example 1, using the compound described in Step A of Example 3 and 6-(2-chloro-ethyl)-7-methyl-thiazolo[3,2-a]pyrimidin-5-one as starting materials. The product obtained is converted into a salt using fumaric acid.

Elemental Microanalysis:

|  | C % | H % | N % | S % |
|---|---|---|---|---|
| calculated | 63.03 | 5.10 | 7.87 | 6.01 |
| found | 62.91 | 5.08 | 7.77 | 5.83 |

EXAMPLE 5

3-[3-((3aα,11cα)-1,3a,4,11c-Tetrahydrobenzo[5,6]chromeno[3,4-c]-pyrrol-2(3H)-yl)propyl]-2-methyl-4H-pyrido[1,2-a]pyrimidin-4-one Hemifumarate Step A: 3-(2-Methyl)-4-oxo-pyrido[1,2-a]pyrimidin-3-yl)-propionaldehyde To 60 mmol of 3-(2-chloro-ethyl)-2-methyl-pyrido[1,2-a]pyrimidin-4-one (prepared according to Liebigs Ann. Chem. 1973, 103-110) in 140 ml of dimethyl sulphoxide there are added 120 mmol of potassium cyanide. The reaction mixture is heated at 100° C. for 3 hours. After evaporating off the dimethyl sulphoxide, the crude product is taken up in dichloromethane and water, and extracted with dichloromethane. The organic phases are washed and dried. The residue is purified by chromatography on silica (eluant: dichloromethane/methanol 95/5) and the product obtained is then dissolved in 100 ml of dichloromethane. The mixture is cooled to −70° C.; 120 mmol of diisobutyl aluminium hydride are introduced. After stirring for 2 hours at that temperature, the mixture is treated with 50 ml of methanol and 100 ml of water; the organic phase is then washed and dried to yield the expected product.

Step B: 3-[3-((3aα,11cα)-1,3a,4,11c-Tetrahydrobenzo[5,6]chromeno[3,4-c]pyrrol-2(3H)-yl)propyl]-2-methyl-4H-pyrido[1,2-a]pyrimidin-4-one Hemifumarate To 10 mmol of the compound described in Step A of Example 3 dissolved in 1,2-dichloroethane there are added 10 mmol of the compound obtained in the previous Step followed by 14 mmol of sodium triacetoxyborohydride. After stirring for 4 hours, water is added; the reaction mixture is then separated and extracted with dichloromethane. The combined organic phases are dried and then filtered and evaporated. The residue thereby obtained is purified by chromatography on silica (eluant: dichloromethane/methanol 95/5) to yield the expected product after conversion into a salt using fumaric acid.

Elemental Microanalysis:

|  | C % | H % | N % |
|---|---|---|---|
| calculated | 72.03 | 6.04 | 8.69 |
| found | 71.68 | 5.95 | 8.59 |

EXAMPLE 6

3-{2-[(3aα,11cα)-1,3,3a,4,5,11c-Hexahydro-2H-naphtho[1,2-e]-isoindol-2-yl]ethyl}-2-methyl-4H-pyrido[1,2-a]pyrimidin-4-one Fumarate Step A: 2-Chloromethyl-naphthalene To 1.26 mol of naphth-2-yl-methanol in 1.5 liters of toluene there are slowly added 3.8 mol of thionyl chloride. The mixture is then heated at reflux for two hours. After cooling, the solvent is evaporated off. The crude product is taken up in toluene twice and evaporated. The oil obtained is taken up in dichloromethane, washed and dried. After filtering and evaporating, the oil obtained is distilled to yield the expected product.
Boiling Point: 118° C. under 0.09 mm of Hg Step B: Ethyl 4-(2-naphthyl)-2-butenoate To 863 mmol of the compound obtained in the previous Step in 206 ml of tri-butylamine there are added 1.07 mol of ethyl acrylate and 10 mmol of palladium acetate. The reaction mixture is heated at reflux for five hours. After cooling, the mixture is hydrolysed and extracted once with dichloromethane. The organic phase is washed with 1N hydrochloric acid solution and then with water before being dried. The product is purified by chromatography on silica (eluant: cyclohexane/ethyl acetate 95/5) to yield the expected product.

Step C: Ethyl 4-(2-naphthyl)-2-butanoate

To 490 mmol of the compound obtained in the previous Step in 3 liters of ethanol there are added 7 grams of 10% palladium-on-carbon. The mixture is then placed under an atmosphere of hydrogen. After the theoretical amount of hydrogen has been absorbed, the mixture is filtered and the solvent is evaporated off to yield the expected product.

Step D: 4-(2-Naphthyl)-2-butanoic Acid

To 484 mmol of the compound obtained in the previous Step in 1.5 liters of ethanol there are added 490 ml of a titrated 2N sodium hydroxide solution. The mixture is heated and maintained at reflux for one hour. The ethanol is then evaporated off. The pH is adjusted to a value of 5–6 using 1N hydrochloric acid. The precipitate formed is filtered off and washed with water to yield the expected product.

Step E: 2,3-Dihydro-4(1H)-phenanthrenone

To 550 g of polyphosphoric acid there are added 240 mmol of the compound obtained in the previous Step. The reaction mixture is heated at 80° C. for 3 hours and then poured onto ice. After stirring for one hour, the precipitate formed is filtered off, washed with water and dried to yield the expected product.

Step F: 1,2-Dihydro-4-phenanthrene-carbonitrile

To 207 mmol of the compound obtained in the previous Step in 500 ml of tetrahydrofuran there are added, in succession, 243 mmol of trimethylsilane cyanide and then 16 mmol of a 0.5M solution of lithium cyanide in dimethylformamide. The reaction mixture is stirred for 2 hours and then poured onto ice and extracted 4 times with ether. The organic phases are collected and washed with water before being dried. After filtering, the solvents are evaporated off. The residue is dissolved in 325 ml of pyridine. 42 ml of POCl₃ are added. The mixture is heated at 100° C. for 3 hours and then cooled before being poured onto 400 ml of ice-cold hydrochloric acid. After adding dichloromethane, the mixture is separated and then extracted with dichloromethane. The combined organic phases are washed and then dried. After filtering, the solvents are evaporated off. The residue obtained is purified by chromatography on silica (eluant: cyclohexane/dichloromethane: 70/30) to yield the expected product.

Step G: 1,2,3,4-Tetrahydro-phenanthrene-3,4-dicarbonitrile

To 87 mmol of acetic acid there are added 105 mmol of a 0.5M solution of lithium cyanide and then, at 5° C., 82 mmol of the compound obtained in the previous Step dissolved in 500 ml of dimethylformamide. The reaction mixture is heated at 100° C. for two hours before being cooled and then dried and poured onto ice. The precipitate obtained is filtered off and washed to yield the expected product.

Step H: 1,2,3,4-Tetrahydro-phenanthrene-3,4-dicarboxylic Acid

To 68 mmol of the compound obtained in the previous Step there are added, in succession, 42 ml of acetic acid and then 84 ml of concentrated hydrochloric acid. The reaction mixture is heated at reflux for 5 days before being cooled and poured into one liter of water. The product is extracted with ethyl acetate. The organic phases are collected and dried. After filtering and evaporating off the solvent, the residue obtained is purified by chromatography (eluant: dichloromethane/methanol/acetic acid: 95/5/0.5) to yield the expected product.

Step I: (3aα,11cα)-3a,4,5,11c-Tetrahydrophenanthro[3,4-c]furan-1,3-dione

To 37 mmol of the compound obtained in the previous Step there are added 1.67 mol of acetic anhydride. The reaction mixture is heated at reflux for 2 hours and then evaporated to dryness. The residue obtained is triturated in ether to yield the expected product in the form of crystals.

Step J: (3aα,11cα)-2-Benzyl-3a,4,5,11c-tetrahydro-1H-naphtho[1,2-e]isoindole-1,3(2H)-dione To 18 mmol of the compound obtained in the previous Step in 400 ml of toluene there are added 18 mmol of benzylamine. The reaction mixture is heated at reflux for 30 hours. 70 ml of 0.1N hydrochloric acid solution are added. The mixture is separated. The organic phase is dried, filtered and then evaporated. The residue obtained is purified by chromatography on silica (eluant: dichloromethane/cyclohexane: 60/40) to yield the expected product.

Step K: (3aα,11cα)-2-Benzyl-2,3,3a,4,5,11c-hexahydro-1H-naphtho[1,2-e]-isoindole Hydrochloride 180 ml of anhydrous ether are poured over 93 mmol of lithium aluminium hydride. After cooling to −10° C., 15.5 mmol of the compound obtained in the previous Step dissolved in 250 ml of dichloromethane are added. The reaction mixture is stirred at ambient temperature for 2 hours and is then cooled to −10° C. 90 ml of water are added slowly. The gel obtained is filtered off and washed with copious amounts of dichloromethane. The organic phases and the filtrate are combined and separated. The organic phase is dried, filtered and then evaporated. The residue obtained is purified by chromatography on silica (eluant: cyclohexane/ethyl acetate 80/20). The product obtained is converted into a salt using hydrochloric acid.

Elemental Microanalysis:

|  | C % | H % | N % | Cl % |
|---|---|---|---|---|
| calculated | 78.95 | 6.91 | 4.00 | 10.13 |
| found | 78.60 | 6.99 | 4.28 | 10.04 |

Step L: 3-{2-[(3aα,11cα)-1,3,3a,4,5,11c-Hexahydro-2H-naphtho[1,2-e]isoindol-2-yl]ethyl}-2-methyl-4H-pyrido[1,2-a]pyrimidin-4-one Fumarate The expected product is obtained according to the procedure described in Steps F and G of Example 1, starting from the compound obtained in the previous Step. The product obtained is converted into a salt using fumaric acid.

Elemental Microanalysis:

|  | C % | H % | N % |
|---|---|---|---|
| calculated | 70.49 | 5.88 | 7.85 |
| found | 70.84 | 5.94 | 7.99 |

EXAMPLE 7

3-[2-((3aα,9bβ)-6,8-Dimethoxy-7-methyl-1,3a,4,9b-tetrahydrochromeno[3,4-c]pyrrol-2(3H)-yl)-ethyl]-2-methyl-4H-pyrido[1,2-a]-pyrimidin-4-one Sesquifumarate Step A: trans-(3,5-Dimethoxy-6-hydroxy-6-methyl)-cinnamic Acid Methyl Ester To 70 mmol of the compound obtained in Step B of Example 2 in 100 ml of methanol there are slowly added 205 mmol of a 30% solution of sodium methylate in methanol. The reaction mixture is heated at reflux for 4 hours before being hydrolysed using 1N hydrochloric acid solution. The precipitate is filtered off, washed with water and dried to yield the expected product.

Step B: (3aα,9bβ)-2-Benzyl-6,8-dimethoxy-7-methyl-1,2,3,3a,4,9b-hexahydrochromeno[3,4-c]pyrrole Hydrochloride The expected product is obtained according to the procedure described in Steps C and D of Example 2, starting from the compound obtained in the previous Step.

Elemental Microanalysis:

|  | C % | H % | N % | Cl % |
|---|---|---|---|---|
| calculated | 67.10 | 6.97 | 3.73 | 9.43 |
| found | 67.15 | 7.13 | 3.76 | 9.73 |

Step C: 3-[2-((3aα,9bβ)-6,8-Dimethoxy-7-methyl-1,3a,4,9b-tetrahydrochromeno[3,4-c]pyrrol-2(3H)-yl)-ethyl]-2-methyl-4H-pyrido[1,2-a]-pyrimidin-4-one Sesquifumarate The expected product is obtained according to the procedure described in Steps F and G of Example 1, starting from the compound obtained in the previous Step. The product obtained is converted into a salt using fumaric acid.

EXAMPLE 8

3-[2-(1,3a,4,11c-Tetrahydrobenzo[5,6]chromeno[3,4-c]pyrrol-2(3H)-yl)ethyl]-7-chloro-2-methyl-4H-pyrido[1,2-a]pyrimidin-4-one Fumarate Step A: 7-Chloro-3-(2-chloroethyl)-2-methyl-4H-pyrido[1,2-a]pyrimidin-4-one The product is prepared according to a procedure described in the literature (Liebigs Ann. Chem. 1973, 103-110), using 2-amino-5-chloropyridine as starting reagent.

Step B: 3-[2-(1,3a,4,11c-Tetrahydrobenzo[5,6]chromeno[3,4-c]pyrrol-2(3H)-yl) ethyl]-7-chloro-2-methyl-4H-pyrido[1,2-a]pyrimidin-4-one Fumarate The expected product is obtained according to the procedure described in Step G of Example 1, using the compound described in the previous Step and the compound obtained in Step A of Example 3 (the product is converted into a salt using fumaric acid).

Elemental Microanalysis:

|  | C % | H % | N % | Cl % |
|---|---|---|---|---|
| calculated | 63.21 | 4.97 | 7.18 | 6.08 |
| found | 62.98 | 5.08 | 7.03 | 6.19 |

EXAMPLE 9

3-[2-((3aα,9bα)-6,8-Dimethoxy-7-methyl-1,3a,4,9b-tetrahydrochromeno[3,4-c]pyrrol-2(3H)-yl)ethyl]-7-chloro-2-methyl-4H-pyrido[1,2-a]pyrimidin-4-one Fumarate The expected product is obtained according to the procedure described in Example 2, using 7-chloro-3-(2-chloroethyl)-2-methyl-4H-pyrido[1,2-a]pyrimidin-4-one prepared in Step A of Example 8 as starting material instead of 3-(2-chloroethyl)-2-methyl-4H-pyrido[1,2-a]-pyrimidin-4-one. The product obtained is converted into a salt using fumaric acid.

Elemental Microanalysis:

|  | C % | H % | N % | Cl % |
|---|---|---|---|---|
| calculated | 59.44 | 5.5 | 7.17 | 6.05 |
| found | 58.94 | 5.43 | 6.97 | 6.34 |

EXAMPLE 10

6-[2-((3aα,9bα)-6-Methoxy-1,3a,4,9b-tetrahydrochromeno[3,4-c]-pyrrol-2(3H)-yl)ethyl]-7-methyl-5H-[1,3]thiazolo[3,2-a]pyrimidin-5-one Fumarate Step A: (3aα,9bα)-6-Methoxy-1,2,3,3a,4,9b-hexahydrochromeno[3,4-c]pyrrole The product is prepared as in Steps A-F of Example 1, starting from cis-(2,3 dimethoxy)cinnamic acid.

Step B: 6-[2-((3aα,9bα)-6-Methoxy-1,3a,4,9b-tetrahydrochromeno[3,4-c]pyrrol-2(3H)-yl)ethyl]-7-methyl-5H-[1,3]thiazolo[3,2-a]pyrimidin-5-one Fumarate The expected product is obtained starting from the compound prepared in the previous Step and following the procedure used in Step G of Example 1, using 6-(2-chloroethyl)-7-methyl-5H-[1,3]thiazolo[3,2-a]pyrimidin-5-one. The product is converted into a salt using fumaric acid.

Elemental Microanalysis:

|  | C % | H % | N % | S % |
|---|---|---|---|---|
| calculated | 58.47 | 5.30 | 8.18 | 6.24 |
| found | 58.78 | 5.22 | 8.27 | 6.20 |

EXAMPLE 11

3-[2-((3aα,9bα)-6-Methoxy-1,3a,4,9b-tetrahydrochromeno[3,4-c]-pyrrol-2(3H)-yl)ethyl]-2-methyl-4H-pyrido[1,2-a]pyrimidin-4-one Fumarate The expected product is obtained according to the procedure described in Example 1, Step G, using the compound described in Step A of Example 10 and 3-(2-chloroethyl)-2-methyl-4H-pyrido[1,2-a]pyrimidin-4-one as starting materials. The product obtained is converted into a salt using fumaric acid.

Elemental Microanalysis:

|  | C % | H % | N % |
|---|---|---|---|
| calculated | 63.90 | 5.76 | 8.28 |
| found | 63.03 | 5.77 | 7.91 |

EXAMPLE 12

3-[2-((3aα,9bα)-6Methoxy-1,3a,4,9b-tetrahydrochromeno[3,4-c]-pyrrol-2(3H)-yl)ethyl]-7-bromo-2-methyl-4H-pyrido[1,2-a]-pyrimidin-4-one Fumarate Step A: 3-(2-Chloroethyl)-7-bromo-2-methyl-4H-pyrido-[1,2-a]pyrimidin-4-one The product is prepared according to the procedure described in Step A of Example 8, using 2-amino-5-bromopyridine as starting reagent.

Step B: 3-[2-((3aα,9bα)-6-Methoxy-1,3a,4,9b-tetrahydrochromeno[3,4-c]pyrrol-2(3H)-yl)ethyl]-7-bromo-2-methyl-4H-pyrido[1,2-a]pyrimidin-4-one Fumarate The expected product is obtained according to the procedure described in Example 11, starting from the compound of Example 10 and the pyrimidinone prepared in the previous Step. The product is converted into a salt using fumaric acid.

Elemental Microanalysis:

|  | C % | H % | N % | Br % |
|---|---|---|---|---|
| calculated | 55.30 | 4.81 | 7.17 | 13.63 |
| found | 55.02 | 4.75 | 7.12 | 13.81 |

EXAMPLE 13

3-[2-((3aα,11cα)-1,3a,4,11c-Tetrahydrobenzo[5,6]chromeno[3,4-c]-pyrrol-2(3H)-yl)ethyl]-2,7-dimethyl-4H-pyrido[1,2-a]pyrimidin-4-one Fumarate Step A: 3-(2-Chloroethyl)-2,7-dimethyl-4H-pyrido[1,2-a]pyrimidin-4-one The product is prepared according to the procedure described in Step A of Example 8, using 2-amino-5-methylpyridine as starting reagent.

Step B: 3-[2-((3aα, 11cα)-1,3a,4,11c-Tetrahydrobenzo[5,6]chromeno[3,4-c]pyrrol-2(3H)-yl)ethyl]-2,7-dimethyl-4H-pyrido[1,2-a]pyrimidin-4-one Fumarate The expected product is obtained according to the procedure described in Step G of Example 1, starting from the compound prepared in the previous Step and the compound of Step A of Example 3. The product is converted into a salt using fumaric acid.

Elemental Microanalysis:

|  | C % | H % | N % |
|---|---|---|---|
| calculated | 68.75 | 5.77 | 7.76 |
| found | 67.96 | 5.60 | 7.67 |

EXAMPLE 14

3-[2-((3aα,9bα)-6,8-Dimethoxy-7-methyl-1,3a,4,9b-tetrahydrochromeno[3,4-c]pyrrol-2(3H)-yl)ethyl]-2,7-dimethyl-4H-pyrido-[1,2-a]pyrimidin-4-one Fumarate The expected product is obtained according to the procedure described in Example 1, Step G, using the compound obtained in Step A of Example 13 and the product of Step E of Example 2 as starting materials. The product is converted into a salt using fumaric acid.

Elemental Microanalysis:

|  | C % | H % | N % |
|---|---|---|---|
| calculated | 63.70 | 6.24 | 7.43 |
| found | 63.57 | 6.09 | 7.36 |

EXAMPLE 15

3-[2-((3aα,11cα)-1,3a,4,11c-Tetrahydrobenzo[5,6]chromeno[3,4-c]-pyrrol-2(3H)-yl)ethyl]-7-bromo-2-methyl-4H-pyrido[1,2-a]-pyrimidin-4-one Fumarate The expected product is obtained according to the procedure described in Example 1, Step G, using the compound obtained in Step A of Example 3 together with the product obtained in Step A of Example 12 as starting materials. The product is converted into a salt using fumaric acid.

Elemental Microanalysis:

|  | C % | H % | N % | Br % |
|---|---|---|---|---|
| calculated | 59.41 | 4.65 | 6.93 | 13.18 |
| found | 59.04 | 4.69 | 6.81 | 12.93 |

EXAMPLE 16

3-[2-((3aα,9bα)-6-Hydroxy-8-methoxy-7-methyl-1,3a,4,9b-tetrahydrochromeno[3,4-c]pyrrol-2(3H)-yl)ethyl]-2-methyl-4H-pyrido[1,2-a]pyrimidin-4-one Fumarate Step A: (3aα,9bα)-2-Benzyl-8-methoxy-7-methyl-1,2,3,3a,4,9b-hexahydrochromeno-[3,4-c]pyrrol-6-ol At 0° C., add 64 ml of a molar solution of boron tribromide in dichloromethane to a solution of 20 g of the compound described in Step D of Example 2. After stirring for three hours at 20° C., hydrolyse using 200 ml of saturated sodium hydrogen carbonate solution and separate off the organic phase. The residue obtained is purified by chromatography on silica gel using a mixture of dichloromethane/methanol: 98/2 as eluant.

Step B: (3aα,9bα)-8-Methoxy-7-methyl-1,2,3,3a,4,9b-hexahydrochromeno[3,4-c]-pyrrol-6-ol The product prepared in the previous Step is debenzylated by applying the procedure described in Step F of Example 1.

Step C: 3-[2-((3aα,9bα)-6-Hydroxy-8-methoxy-7-methyl-1,3a,4,9b-tetrahydrochrom 3,4-c]pyrrol-2(3H)-yl) ethyl]-2-methyl-4H-pyrido[1,2-a]-pyrimidin-4-one Fumarate The expected product is obtained according to the procedure described in Step G of Example 1, using the compound described in the previous Step and 3-(2-chloroethyl)-2-methyl-4H-pyrido[1,2-a]pyrimidin-4-one as starting reagents. The product is converted into a salt using fumaric acid.

Elemental Microanalysis:

|  | C % | H % | N % |
|---|---|---|---|
| calculated | 62.56 | 5.81 | 7.82 |
| found | 61.61 | 5.97 | 7.42 |

EXAMPLE 17

3-[4-(3aα,11cα)-1,3a,4,11c-Tetrahydrobenzo[5,6]chromeno[3,4-c]pyrrol-2(3H)-yl)butyl]-2-methyl-4H-pyrido[1,2-a]pyrimidin-4-one, Fumarate Step A: 3-(3-Butenyl)-2-methyl-4H-pyrido[1,2-a]pyrimidin-4-one Heat a mixture of 5.7 g of methyl 2-acetyl-5-hexenoate, 3.15 g of 2-aminopyridine and 0.65 g of polyphosphoric acid at 160° C. for 2 hours. Then add, in the cold state, 30 ml of water and extract the mixture using dichloromethane. The residue obtained after evaporating off the solvent is purified by chromatography on silica gel, using a mixture of dichloromethane/methanol: 98/2 as eluant.

Step B: 3-Butyl-2-methyl-4H-pyrido[1,2-a]pyrimidin-4-one

Add 55.2 ml of a molar solution of borane in tetrahydrofuran to a solution of 5.4 g of the product obtained in the previous Step in 100 ml of tetrahydrofuran. After one hour, cool to 0° C. and add 10 ml of water and then 25.4 g of sodium borate. Stir for one hour and then concentrate the mixture; take up the residue in 100 ml of water and extract with dichloromethane. After evaporating off the solvent, the residue obtained is purified by chromatography on silica gel, using a mixture of dichloromethane/methanol: 98/2 as eluant.

Step C: 4-(2-Methyl-4-oxo-4H-pyrido[1,2-a]pyrimidin-3-yl)butanal

Heat a mixture of 4.5 g of the product obtained in the previous Step together with 8.1 g of 1-hydroxy-1-oxo-benzo[d][1,2]iodoxol-3-one in 200 ml of tetrahydrofuran at reflux for 3 hours. Filter in the cold state and concentrate the filtrate.

Step D: 3-[4-(3aα,11cα)-1,3a,4,11c-Tetrahydrobenzo[5,6]chromeno[3,4-c]pyrrol-2(3H)-yl)-butyl]-2-methyl-4H-pyrido[1,2-a]pyrimidin-4-one The remainder of the synthesis is performed by applying the procedure described in Step B of Example 5, starting from the aldehyde obtained in the previous Step. The product is converted into a salt using fumaric acid.

Elemental Microanalysis:

|  | C % | H % | N % |
|---|---|---|---|
| calculated | 68.06 | 5.89 | 7.26 |
| found | 67.25 | 5.85 | 6.82 |

EXAMPLE 18

3-[2-((3aα,11cα)-1,3a,4,11c-Tetrahydrobenzo[5,6]chromeno[3,4-c]-pyrrol-2(3H)-yl)ethyl]-2-methyl-4H-pyrido[1,2-a]pyrimidin-4-one, Fumarate Step A: (3aα,11cα)-1,2,3,3a,4,11c-Hexahydrobenzo[5,6]chromeno[3,4-c]pyrrole Separation of the racemate 1,2,3,3a,4,11c-hexahydrobenzo[5,6]chromeno[3,4-c]pyrrole: Dissolve 53.6 g of product obtained in Step A of Example 3 in 450 ml of ethanol and heat the mixture at reflux. Add a solution of 85.2 g of (+)2,3-dibenzoyl-D-tartaric acid in 450 ml of ethanol. Filter off the precipitate 12 hours later. Recrystallise the precipitate three times from a mixture of ethanol/water: 85/15. The compound is obtained in the form of a base after treatment with aqueous sodium hydroxide solution.

Step B: 3-[2-((3aα,11cα)-1,3a,4,11c-Tetrahydrobenzo[5,6]chromeno[3,4-c]pyrrol-2(3H)-yl)ethyl]-2-methyl-4H-pyrido[1,2-a]pyrimidin-4-one, Fumarate The expected product is obtained according to the procedure described in Step G of Example 1, using the enantiomer prepared in the previous Step and 3-(2-chloroethyl)-2-methyl-4H-pyrido[1,2-a]pyrimidin-4-one as starting materials. The product is converted into a salt using fumaric acid.

Elemental Microanalysis:

|  | C % | H % | N % |
|---|---|---|---|
| calculated | 68.30 | 5.54 | 7.96 |
| found | 68.24 | 5.41 | 8.12 |

EXAMPLE 19

3-[2-((3aβ,11cβ)-1,3a,4,11c-Tetrahydrobenzo[5,6]chromeno[3,4-c]-pyrrol-2(3H)-yl)ethyl]-2-methyl-4H-pyrido[1,2-a]pyrimidin-4-one, Fumarate Step A: (3aβ,11cβ)-1,2,3,3a,4,11c-Hexahydrobenzo[5,6]chromeno[3,4-c]pyrrole Separation of the racemate: 1,2,3,3a,4,11c-hexahydrobenzo[5,6]chromeno[3,4-c]pyrrole Dissolve 10.3 g of product obtained in Step A of Example 3 in 200 ml of ethanol and heat the mixture at reflux. Add a solution of 16.4 g of (−)2,3-dibenzoyl-L-tartaric acid in 200 ml of ethanol. Filter off the precipitate 12 hours later. Recrystallise the precipitate three times from a mixture of ethanol/water: 85/15. The compound is obtained in the form of a base after treatment with aqueous sodium hydroxide solution.

Step B: 3-[2-((3aβ,11cβ)-1,3a,4,11c-Tetrahydrobenzo[5,6]chromeno[3,4-c]pyrrol-2(3H)-yl)ethyl]-2-methyl-4H-pyrido[1,2-a]pyrimidin-4-one, Fumarate The expected product is obtained according to the procedure described in Step G of Example 1, using the enantiomer prepared in the previous Step and 3-(2-chloroethyl)-2-methyl-4H-pyrido[1,2-a]pyrimidin-4-one as starting materials.

The product is converted into a salt using fumaric acid.

Elemental Microanalysis:

|  | C % | H % | N % |
|---|---|---|---|
| calculated | 68.30 | 5.54 | 7.96 |
| found | 68.85 | 5.45 | 7.81 |

EXAMPLE 20

3-[2-((3aα,9bα)-6,8-Dimethoxy-7-propyl-1,3a,4,9b-tetrahydrochromeno[3,4-c]pyrrol-2(3H)-yl)ethyl]-2-methyl-4H-pyrido[1,2-a]-pyrimidin-4-one Fumarate Step A: 2-Allyloxy-4-methoxybenzaldehyde To a solution of 100 g of 2-hydroxy-4-methoxybenzaldehyde in 2 liters of acetone add 79.5 ml of allyl bromide and then, gradually, 272 g of potassium carbonate. Heat at reflux for 4 hours and then filter; concentrate the filtrate in vacuo, take up the residue in 1 liter of dichloromethane and wash the solution with 1N sodium hydroxide solution and then with saturated sodium chloride solution. Dry over magnesium sulphate and concentrate in vacuo.

Step B: 3-Allyl-2-hydroxy-4-methoxybenzaldehyde

Heat a solution of 125 g of the product obtained in Step A in 300 ml of N,N-dimethylaniline at 200° C. for 15 hours. Then evaporate off the solvent in vacuo and take up the residue in 1 liter of isopropyl ether; extract the solution 10 times using 100 ml of 1N sodium hydroxide solution each time and then acidify the combined extracts using 3N hydrochloric acid. Then extract the aqueous acid solution with dichloromethane, and dry and concentrate the organic phase.

Step C: 3-Allyl-2,4-dimethoxybenzaldehyde

Heat a mixture of 108 g of the product obtained in the previous Step, 74.4 g of dimethyl sulphate and 233 g of potassium carbonate in 2 liters of acetone at reflux for 5 hours. Filter in the cold state and concentrate the solution obtained. The residue is taken up in isopropyl ether and is washed with saturated sodium hydrogen carbonate solution and then with water. Dry over magnesium sulphate and evaporate off the solvent in vacuo. The residue is purified by chromatography on silica gel using a mixture of cyclohexane/ethyl acetate: 96/4 as eluant.

Step D: 2,4-Dimethoxy-3-propylbenzaldehyde

Hydrogenate 64 g of the product obtained in Step C, at ambient temperature and under atmospheric pressure, using 35 g of Wilkinson's catalyst [tris(triphenylphosphine) rhodium chloride] in 500 ml of benzene. The product is purified by chromatography on silica gel, using a mixture of cyclohexane/ethyl acetate: 92/8 as eluant.

Step E: 3-[2-((3aα,9bα)-6,8-Dimethoxy-7-propyl-1,3a,4,9b-tetrahydrochromeno-[3,4-c]pyrrol-2(3H)-yl)ethyl]-2-methyl-4H-pyrido[1,2-a]pyrimidin-4-one Fumarate The remainder of the synthesis is performed by applying the procedures described in Example 2 (Steps A to F) using the aldehyde obtained in the previous Step as starting reagent. The product is converted into a salt using fumaric acid.

Elemental Microanalysis

|  | C % | H % | N % |
|---|---|---|---|
| calculated | 64.24 | 6.43 | 7.25 |
| found | 63.33 | 6.30 | 7.05 |

EXAMPLE 21

3-[2-((3aα,11cα)-1,3a,4,11c-Tetrahydrobenzo[5,6] chromeno[3,4-c]-pyrrol-2(3H)-yl)ethyl]-7-chloro-2-methyl-4H-pyrido[1,2-a]pyrimidin-4-one Fumarate Step A: (7-Chloro-2-methyl-4-oxo-4H-pyrido[1,2-a] pyrimidin-3-yl)acetaldehyde The product is prepared by following the procedure described in Step C of Example 18, using 7-chloro-3-(2-hydroxyethyl)-2-methyl-4H-pyrido[1,2-a]pyrimidin-4-one as starting substrate obtained following a procedure described in the literature (Liebigs Ann. Chem. 1973, 103–110).

Step B: 3-[2-((3aα,11cα)-1,3a,4,11c-Tetrahydrobenzo[5,6] chromeno[3,4-c]pyrrol-2(3H)-yl)ethyl]-7-chloro-2-methyl-4H-pyrido[1,2-a]pyrimidin-4-one Fumarate The expected product is obtained according to the procedure described in Step B of Example 5, using the compound prepared in Step A of Example 19 and the aldehyde prepared in the previous Step. The product is converted into a salt using fumaric acid.

Elemental Microanalysis:

|  | C % | H % | N % | Cl % |
|---|---|---|---|---|
| calculated | 64.11 | 5.02 | 7.48 | 6.31 |
| found | 63.82 | 5.02 | 7.35 | 6.63 |

EXAMPLE 22

3-[2-((3aβ,11cβ)-1,3a,4,11c-Tetrahydrobenzo[5,6] chromeno[3,4-c]-pyrrol-2(3H)-yl)ethyl]-7-chloro-2-methyl-4H-pyrido[1,2-a]pyrimidin-4-one Fumarate The expected product is obtained according to the procedure described in Step B of Example 5, using the compound prepared in Step A of Example 20 and the aldehyde prepared in Step A of Example 22. The product is converted into a salt using fumaric acid.

Elemental Microanalysis

|  | C % | H % | N % | Cl % |
|---|---|---|---|---|
| calculated | 64.11 | 5.02 | 7.48 | 6.31 |
| found | 64.30 | 4.92 | 7.53 | 6.56 |

EXAMPLE 23

3-[2-((3aα,11cα)-1,3a,4,11c-Tetrahydrobenzo[5,6] chromeno[3,4-c]-pyrrol-2(3H)-yl)ethyl]-2-methyl-4-oxo-4H-pyrido[1,2-a]pyrimidine-7-carbonitrile Fumarate To a solution of 1.83 mmol of the compound obtained in Example 15 in 12 ml of dimethylformamide there are added, under an inert atmosphere, 1.1 mmol of zinc cyanide and 0.073 mmol of tetrakis(triphenylphosphine) palladium. Heat the reaction mixture at 90° C. for 12 hours. Evaporate the reaction mixture, take up in methylene chloride, filter over Celite and then evaporate. The residue obtained is purified by chromatography on silica (eluant: dichloromethane/methanol: 95/5). The product is converted into a salt using fumaric acid.

Elemental Microanalysis:

|  | C % | H % | N % |
|---|---|---|---|
| calculated | 68.52 | 5.18 | 10.58 |
| found | 68.63 | 5.05 | 10.58 |

EXAMPLE 24

3-[2-((3aα,11cα)-1,3a,4,11c-Tetrahydrobenzo[5,6]chromeno[3,4-c]-pyrrol-2(3H)-yl)ethyl]-2-methyl-7-(2-thienyl)-4H-pyrido[1,2-a]-pyrimidin-4-one Fumarate Step A: 3-(2-Hydroxyethyl)-2-methyl-7-(2-thienyl)-4H-pyrido[1,2-a]pyrimidin-4-one In a round-bottom flask under a current of argon, mix 5 g of 7-bromo-3-(2-hydroxyethyl)-2-methyl-4H-pyrido[1,2-a]pyrimidin-4-one, 6.2 ml of tributyl-thiophen-2-yl-stannane, 1 g of tetrakis(triphenylphosphine) palladium and 250 ml of N-methylpyrrolidone. Heat the solution at 130° C. for 2 hours and then evaporate off the solvent in vacuo; take up the residue in 200 ml of dichloromethane, wash the solution with 10% potassium fluoride solution, filter, separate off the organic phase and wash it with water. After drying over magnesium sulphate and evaporation, the residue obtained is purified by chromatography on silica gel using a mixture of dichloromethane/methanol: 95/5 as eluant.

Step B: 3-(2-Chloroethyl)-2-methyl-7-(2-thienyl)-4H-pyrido[1,2-a]pyrimidin-4-one The product of the previous Step is converted into the chlorinated compound by applying a procedure described in the literature (Liebigs Ann. Chem. 1973, 103–110).

Step C: 3-[2-((3aα,11cα)-1,3a,4,11c-Tetrahydrobenzo[5,6]chromeno[3,4-c]pyrrol -2(3H)-yl)ethyl]-2-methyl-7-(2-thienyl)-4H-pyrido[1,2-a]pyrimidin-4-one Fumarate The remainder of the synthesis is performed by applying the procedure described in Example 1 (Step G), using the product obtained in the previous Step instead of 3-(2-chloroethyl)-2-methylpyrido[1,2-a]pyrimidin-4-one. The product is converted into a salt using fumaric acid.

Elemental Microanalysis:

|  | C % | H % | N % | S % |
|---|---|---|---|---|
| calculated | 66.98 | 5.12 | 6.89 | 5.26 |
| found | 66.02 | 5.07 | 6.85 | 4.94 |

EXAMPLE 25

3-[2-((3aβ,11cα)-1,3a,4,11c-Tetrahydrobenzo[5,6]chromeno[3,4-c]-pyrrol-2(3H)-yl)ethyl]-7-chloro-2-methyl-4H-pyrido[1,2-a]pyrimidin-4-one Hemifumarate Step A: (3aβ,11cα)-1,2,3,3a,4,11c-Hexahydrobenzo[5,6]chromeno[3,4-c]pyrrole The compound is obtained by following the same experimental protocol as that described in the Patent Application EP 691 342 (Example 33).

Step B: 3-[2-((3aβ,11cα)-1,3a,4,11c-Tetrahydrobenzo[5,6]chromeno[3,4-c]pyrrol-2(3H)-yl)ethyl]-7-chloro-2-methyl-4H-pyrido[1,2-a]pyrimidin-4-one hemifumarate The expected product is obtained according to the procedure described in Step G of Example 1, using the compound described in the previous Step and the compound obtained in Step A of Example 8 (the product is converted into a salt using fumaric acid).

Elemental Microanalysis:

|  | C % | H % | N % | Cl % |
|---|---|---|---|---|
| calculated | 66.16 | 5.16 | 8.15 | 6.88 |
| found | 66.33 | 5.10 | 8.31 | 7.40 |

EXAMPLE 26

6-[2-((3aβ,11cα)-1,3a,4,11c-Tetrahydrobenzo[5,6]chromeno[3,4-c]-pyrrol-2(3H)-yl)ethyl]-7-methyl-5H-[1,3]thiazolo[3,2-a]pyrimidin-5-one Hemifumarate The expected product is obtained according to the procedure described in Step G of Example 1, using the compound obtained in Step A of Example 26 together with 6-(2-chloroethyl)-7-methyl-5H-[1,3]thiazolo[3,2-a]pyrimidin-5-one (the product is converted into a salt using fumaric acid).

Elemental Microanalysis:

|  | C % | H % | N % | Cl % |
|---|---|---|---|---|
| calculated | 65.09 | 5.26 | 8.63 | 6.58 |
| found | 64.98 | 5.28 | 8.61 | 6.67 |

EXAMPLE 27

3-[2-((3aβ,11cα)-1,3a,4,11c-Tetrahydrobenzo[5,6]chromeno[3,4-c]-pyrrol-2(3H)-yl)ethyl]-2-methyl-4H-pyrido[1,2-a]pyrimidin-4-one hemifumarate The expected product is obtained according to the procedure described in Step G of Example 1, using the compound described in Step A of Example 26 together with 3-(2-chloroethyl)-2-methylpyrido[1,2-a]pyrimidin-4-one (the product is converted into a salt using fumaric acid).

Elemental Microanalysis:

|  | C % | H % | N % |
|---|---|---|---|
| calculated | 70.90 | 5.74 | 8.73 |
| found | 70.99 | 5.70 | 8.77 |

Pharmacological Study

EXAMPLE A

Penile Erection Test in the Rat

This test allows evaluation of the capacity of pharmacological agents to inhibit penile erections caused by administration of a selective $5\text{-}HT_{2c}$ agonist, RO 60-0175.

Male rats of the Wistar strain weighing 120–140 g on the day of the experiment are placed separately in plexiglass observation boxes immediately after the compound under test or the vehicle has been administered. Thirty minutes later, RO 60-0175 (1.25 mg/kg, subcutaneous) is administered to the animals and the number of erections occurring during the next 30 minutes is counted.

Results: It appears that the compounds of the invention are capable of inhibiting the penile erections caused by administration of the selective 5-$HT_{2c}$ agonist. They accordingly have an antagonist character with respect to 5-$HT_{2c}$ receptors. By way of example, the compound of Example 3 has an inhibitory dose 50 ($ID_{50}$) of 2.6 mg/kg, s.c.

EXAMPLE B

Test for Aggressiveness Caused by Isolation, in the Mouse

The animals used are male CD-1 mice. From the time of their arrival, the mice are isolated in individual cages, with free access to food and drink. After a period of one month of isolation, pairs of mice that are stable in terms of aggressiveness are selected by observing the latency period and the number and the duration of attacks when the mice are placed in the presence of one another.

The test is conducted once per week. On the day of the test, each mouse of the pair (resident and intruder) is given an intraperitoneal injection of the vehicle (control animals) or of the compound under test (treated animals) in a volume of 10 ml/kg. After 30 minutes, the intruder mouse is introduced into the cage of the resident mouse. The latency period until the first attack and the number and the duration of attacks are then measured over a period of three minutes. A compound is considered to be specifically anti-aggressive when it reduces the number and the duration of attacks at non-sedative doses.

Results: It appears that the compounds of the invention significantly reduce the number and the duration of attacks. By way of example, the compound of Example 3 has an inhibitory dose 50 ($ID_{50}$) of 7 mg/kg, i.p.

EXAMPLE C

Marble-Burying Test in the Mouse

This test allows evaluation of the capacity of pharmacological agents to inhibit spontaneous marble-burying behaviour in the mouse, the inhibition being predictive of antidepressant and/or anti-impulsive action.

Male mice of the NMRI strain weighing from 20 to 25 g on the day of the experiment are placed individually in Macrolon boxes containing 5 cm of sawdust and covered with a perforated plexiglass plate. Twenty-four "tiger's eye" glass marbles are evenly distributed on the sawdust at the periphery of the box. At the end of 30 minutes' free exploration, the animals are removed from the box and the number of buried marbles is counted.

Results: It appears that the compounds of the invention inhibit the spontaneous marble-burying behaviour in the mouse. By way of example, the compound of Example 3 has an inhibitory dose 50 ($ID_{50}$) of 4.1 mg/kg, s.c.

EXAMPLE D

Determination of the Affinity for $\alpha_2$-Adrenergic Receptors in the Rat

The affinity was determined by competition experiments with [$^3$H]-RX 821,002. The membranes are prepared from the cerebral cortex of the rat and are incubated in triplicate with 0.4 nM [$^3$H]-RX 821,002 and the compound being tested in a final volume of 1.0 ml, for 60 minutes at 22° C. The incubation buffer contains 50 nM TRIS-HCl (pH 7.5), 1 mM EDTA and 100 $\mu$M GppNHp. The non-specific binding is determined using 10 $\mu$M phentolamine.

Data Analysis: At the end of the incubation, the incubation medium is filtered through WHATMAN GF/B filters impregnated with 0.1% of polyethylenimine and washed three times with 5 ml of cooled buffer. The radioactivity retained on the filters is determined by liquid scintillation counting. The binding isotherms are analysed by non-linear regression.

Results: The compounds of the invention interact in specific manner with the $\alpha_2$-adrenergic receptors, with the compound of Example 3, for example, having a $pK_i$ of 7.5.

EXAMPLE E

Pharmaceutical Composition

Preparation formula for 1000 tablets each containing 10 mg of active ingredient

| | |
|---|---|
| Compound of Example 3 | 10 g |
| Hydroxypropyl cellulose | 2 g |
| Wheat starch | 10 g |
| Lactose | 100 g |
| Magnesium stearate | 3 g |
| Talc | 3 g |

We claim:
1. A compound of formula (I):

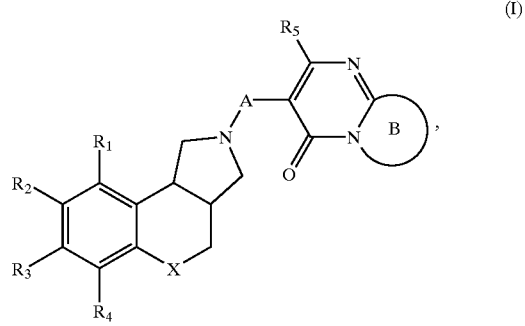

wherein:

$R_1$, $R_2$, $R_3$ and $R_4$, which may be the same or different, each represent a hydrogen atom, a halogen atom or a group selected from linear or branched ($C_1$–$C_6$)alkyl, linear or branched ($C_1$–$C_6$)alkoxy, linear or branched ($C_1$–$C_6$)polyhaloalkyl, hydroxy, cyano, nitro and amino, or $R_1$ with $R_2$, $R_2$ with $R_3$, or $R_3$ with $R_4$, together with the carbon atoms carrying them, form an optionally substituted benzene ring or an optionally substituted heteroaromatic ring, X represents an oxygen atom or a methylene group, A represents a linear or branched ($C_1$–$C_6$)alkylene chain,

represents an unsaturated nitrogen-containing heterocycle optionally substituted by one or two identical or different substituents selected from halogen atoms and linear or branched ($C_1$–$C_6$)alkyl, hydroxy, linear or branched ($C_1$–$C_6$)alkoxy, linear or branched ($C_1$–$C_6$)polyhaloalkyl, cyano, nitro, amino, optionally substituted phenyl, optionally substituted thienyl, optionally substituted furyl and optionally substituted pyrrolyl groups, and $R_5$ represents a linear or branched ($C_1$–$C_6$)alkyl group, its enantiomers and diastereoisomers, and addition salts thereof with a pharmaceutically acceptable acid or base, it being understood that:

- the term "($C_1$–$C_6$)alkyl" denotes a saturated hydrocarbon chain containing from one to six carbon atoms,
- the term "($C_1$–$C_6$)alkoxy" denotes a ($C_1$–$C_6$)alkyl-oxy group containing from one to six carbon atoms,
- the term "($C_1$–$C_6$)alkylene" denotes a bivalent hydrocarbon chain containing from one to six carbon atoms,
- the term ($C_1$–$C_6$)polyhaloalkyl denotes a carbon chain containing from one to six carbon atoms and from 1 to 9 halogen atoms,
- the term "heteroaromatic ring" denotes a 5- or 6-membered aromatic ring containing one, two or three hetero atoms selected from oxygen, nitrogen and sulphur,
- the term "unsaturated nitrogen-containing heterocycle" denotes a 5- to 7-membered unsaturated ring having one, two or three unsaturations and containing one, two or three hetero atoms, one of those hetero atoms being the nitrogen atom and the additional hetero atom(s) optionally present being selected from oxygen, nitrogen and sulphur atoms,
- the term "optionally substituted" applied to the expressions "benzene ring", "heteroaromatic ring", "phenyl", "thienyl", "furyl" or pyrrolyl", and indicates that those groups are optionally substituted by one or two identical or different substituents selected from halogen atoms and linear or branched ($C_1$–$C_6$)alkyl, hydroxy, linear or branched ($C_1$–$C_6$)alkoxy, linear or branched ($C_1$–$C_6$)polyhaloalkyl, cyano, nitro and amino groups.

2. A compound of claim 1 wherein $R_1$, $R_2$, $R_3$ and $R_4$, which may be the same or different, each represent a hydrogen atom or a linear or branched ($C_1$–$C_6$)alkyl, linear or branched ($C_1$–$C_6$)alkoxy or hydroxy group.

3. A compound of claim 1 wherein $R_1$ and $R_2$, together with the carbon atoms carrying them, form a benzene ring and $R_3$ and $R_4$ each represent a hydrogen atom.

4. A compound of claim 1 wherein X represents an oxygen atom.

5. A compound of claim 1 wherein A represents an ethylene, propylene or butylene chain.

6. A compound of claim 1 wherein

represents the group

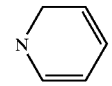

optionally substituted by one or two identical or different substituents selected from halogen atoms and linear or branched ($C_1$–$C_6$)alkyl, hydroxy, linear or branched ($C_1$–$C_6$) alkoxy, linear or branched ($C_1$–$C_6$)polyhaloalkyl, cyano, nitro, amino and thienyl groups.

7. A compound of claim 1 wherein

represents the following group

optionally substituted by one or two identical or different substituents selected from halogen atoms and linear or branched ($C_1$–$C_6$)alkyl, hydroxy, linear or branched ($C_1$–$C_6$) alkoxy, linear or branched ($C_1$–$C_6$)polyhaloalkyl, cyano, nitro and amino groups.

8. A compound of claim 1 wherein A represents an ethylene chain, X represents an oxygen atom, $R_5$ represents a methyl group and

represents the group

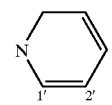

optionally substituted in the 2'-position by a halogen atom or a group selected from linear or branched ($C_1$–$C_6$)alkyl, cyano and thienyl.

9. A compound of claim 1 which is 3-[2-((3aα,9bα)-9-methoxy-1,3a,4,9b-tetrahydrochromeno[3,4-c]pyrrol-2 (3H)-yl)-ethyl]-2-methyl-4H-pyrido[1,2-a]pyrimidin-4-one.

10. A compound of claim 1 which is 3-[2-((3aα,11cα)-1, 3a,4,11c-tetrahydrobenzo[5,6]chromeno[3,4-c]pyrrol-2 (3H)-yl)-ethyl]-2-methyl-4H-pyrido[1,2-a]pyrimidin-4-one.

11. A compound of claim 1 which is 3-[2-((3aβ,11cα)-1, 3a,4,11c-tetrahydrobenzo[5,6]chromeno[3,4-c]pyrrol-2 (3H)-yl)ethyl]-2-methyl-4H-pyrido[1,2-a]pyrimidin-4-one.

12. A pharmaceutical composition useful as a double $α_2$/5-$HT_{2C}$ antagonist comprising as active principle an effective amount of a compound as claimed in claim 1, together with one or more pharmaceutically acceptable excipients or vehicles.

13. A method for treating an animal or human living body afflicted with depression, impulsive behaviour disorders, anxiety, schizophrenia, Parkinson's disease, disturbances of libido, appetite disorders and step disorders requiring a double $\alpha_2/5\text{-HT}_{2c}$ antagonist medicament, comprising the step of administering to the living body an amount of a compound of claim 1 which is effective for alleviation of said condition.

* * * * *

UNITED STATES PATENT AND TRADEMARK OFFICE
CERTIFICATE OF CORRECTION

PATENT NO.    : 6,747,032 B2
DATED         : June 8, 2004
INVENTOR(S)   : Gilbert Lavielle et al.

It is certified that error appears in the above-identified patent and that said Letters Patent is hereby corrected as shown below:

Column 31,
Line 6, "step" should be -- sleep --.

Signed and Sealed this

Thirtieth Day of November, 2004

JON W. DUDAS
*Director of the United States Patent and Trademark Office*